United States Patent [19]

von Wright et al.

[11] Patent Number: 4,977,088

[45] Date of Patent: Dec. 11, 1990

[54] VECTOR PLASMID SUITED FOR SOURING AGENTS, DAIRY SOURING AGENTS IN PARTICULAR

[75] Inventors: Atte J. von Wright, Espoo; Seppo K. Sivelä, Helsinki; Soile S. H. Tynkkynen, Espoo, all of Finland

[73] Assignee: Valio Meijerien Keskusosuusliike, Helsinki, Finland

[21] Appl. No.: 65,882

[22] Filed: Jun. 24, 1987

[30] Foreign Application Priority Data

Jun. 24, 1986 [FI] Finland .................................. 862683

[51] Int. Cl.$^5$ ........................ C12N 1/20; C12N 15/00; C12P 21/00
[52] U.S. Cl. ................................. 435/252.3; 435/69.1; 435/71.1; 435/71.2; 435/172.3; 435/252.32; 435/252.33; 435/252.35; 435/320; 935/29; 935/72; 935/73; 935/74; 935/75
[58] Field of Search ........................ 435/68, 70, 71, 91, 435/172.1, 172.3, 320, 252.3, 252.31–252.35, 69.1, 71.2, 71.3; 935/29, 72, 73, 74

[56] References Cited

FOREIGN PATENT DOCUMENTS 0021468 1/1981 European Pat. Off. ......... 435/172.3

OTHER PUBLICATIONS

Gasson, et al. (1985) Fems Microbiology Letters, 30:193–196.

Kok et al; Appl. Environ. Microbiol. 48: 726 (1984).
Commercial Biotechnology: An International Analysis (Washington, D.C.: U.S. Congress, Office of Technology Assessment, OTA-BA-218, Jan. 1984).
Wallace et al: Science 209: 1396 (1980).
McKay (1983) Antonie van Leeuwenhoek 49:259–274.
Behnke et al., Mol. Gen Genet (1981) 184:115–120.
Weisblum, et al., J. Bacteriol (1979) 137:635–643.
Gasson, J. Bacteriol (1983) 154:1–9.
Kok, et al., (1985) Appl. Environ. Microbiol 50:94–101.

Primary Examiner—James Martinell
Attorney, Agent, or Firm—Kenyon & Kenyon

[57] ABSTRACT

The invention relates to a cloning vector suited for the souring bacteria of dairy industries, which cloning vector is based on a 1.7 kb ClaI fragment of the *Streptococcus lactis* cryptic plasmid pSH71. Therein are inserted a chloramphenicol resistance gene from the *Streptococcus sanguis* plasmid pGB301 and an erythromycin resistance gene from the *Staphylococcus aureus* plasmid pE194, a 0.35 kb fragment from the *Escherichia coli* plasmis pBR322 being inserted therebetween. The size of the cloning vector is 5.0 kb. The cloning vector enables the use of "forced cloning" methods. It possesses a wide host spectrum (group N streptococci, *Escherichia coli, Bacillus subtilis*), and can be applied for improving the souring properties of the group N streptococci and for the preparation of foreign proteins in these bacteria or other hosts.

2 Claims, 1 Drawing Sheet

VECTOR PLASMID SUITED FOR SOURING AGENTS, DAIRY SOURING AGENTS IN PARTICULAR

The invention relates to the application of recombinant DNA technology to souring bacteria, to souring bacteria of dairy industries in particular, a new cloning vector being developed for said bacteria.

Lactic acid bacteria are widely used in souring agents both in food industries and in agriculture. In agriculture, souring inoculations are used in some countries for fodder preservation in particular. Within food industries, souring agents are used particularly in the field of dairy, bakery and meat processing industries. In Finland, the dairy industries are by far the greatest users of souring agents.

Dairy souring agents are used for the production of butter, sour milk, yoghurt, kefir and especially matured cheeses. The most important function of a souring agent is thereby an efficient fermentation of milk sugar (lactose) into lactic acid. In addition, certain souring bacteria produce flavouring agents (diacetyl, acetone, etc.). Enzymes (proteases, peptidases) liberating from souring bacteria are probably also of importance in the maturing process of cheese.

The recombinant DNA technology can be applied extensively in the research and the product development of souring agents. In an attempt to develop souring agents the properties of which are optimized and which are stable and act in a predictable manner, it is important to study the effect of the copy number or the activity of genes encoding important souring properties, for instance, on a desired process. In view of the established use of souring bacteria in foodstuffs as well as their acknowledged safety, it is also possible to consider their use in new industrial processes, e.g. for the preparation of foreign proteins.

The recombinant DNA technology requires both a working transformation system and a suitable vector plasmid. The transformation system should be sufficiently efficient to enable cloning in a desired host organism using ligation mixtures. A good vector, in turn, should have the following properties:
  small size
  high copy number
  easy selectability based on e.g. antibiotic resistance genes
  restriction enzyme cleaving sites suitable for cloning, preferably as so called insertional inactivation sites within the gene
  capable of replicating and capable of expressing selection genes in different hosts.

Among major souring bacteria groups, the genetic properties of the streptococci of the so called group N (*Streptococcus lactic, S. lactis* subsp. diacetylactis and *S. cremoris*) are the best-known.

The most important souring properties of these bacteria (the use of lactose, certain proteinases, production of flavouring agents) are very generally plasmid encoded (10). The streptococci of the group N also have plenty of cryptic plasmids.

A working protoplast transformation technique has recently been developed for the streptococci of the group N (15). Attempts have also been made to develop cloning vectors suited for these bacteria.

In the Netherlands, J. Kok et al. has developed a vector based on the cryptic plasmid pWVOI of *S. cremoris* and having as selection genes the erythromycin and chloramphenicol resistance genes of the *Staphylococcus aureus* plasmids pE194 and pC194. The first-mentioned contains the recognition site of the BClI restriction enzyme. This vector, called pGK12, is of 4.9 kb (1 kb=1000 base pairs), and it further contains the individual cleaving sites of ClaI and HpaII enzymes outside the resistance regions. Besides the streptococci of the group N, the vector also replicates in *Bacillus subtilis* and *Escherichia coli* (6). Using the vector, it has been possible to clone a plasmidorigin protease gene of *S. cremoris* (7).

In England, M. Gasson et al. has developed another vector construction using as a base the *S. lactis* plasmid pSH71. A fragment of the *B. subtilis* plasmid pBD64, which fragment contains chloramphenicol and kanamycin resistance genes, is inserted in the plasmid. The resultant recombinant plasmids (pCK1, pCK17 and pCK21) contain a BglII recognition site within the kanamycin resistance region and, in addition, BamHI, EcoRl, PvuII and XbaI recognition sites otherwhere. Besides these, the plasmids pCK17 and pCK21 further contain a ClaI recognition site. The sizes of the plasmids range from 5.5 to 5.9 kb. Similarly as pGK12, the vectors are capable of replicating in B. subtilis and E. coli (4), too.

The object of the present invention is a new cloning vector which differs from those described above in that it has considerably more versatile cloning possibilities and a higher copy number. The vector plasmid has a wide host spectrum (the group N streptococci, *E. coli, B. subtilis*), and genes originating both from streptococci and other bacteria can be cloned therein and, as a consequence, their expression in different hosts can be examined. In this way it is possible to isolate genes encoding important souring properties and analyse the gene products thereof. Gene variants found to be best suited for use as souring agents can be retransferred in souring agent strains, thus optimizing the genetic composition of utilizeable souring agents. The vector can also be applied to the production of foreign proteins either in the group N streptococci or in more conventional production hosts. The last-mentioned (mainly *B. subtilis* or *E. coli*) can also be used for the mass production of gene products which are of streptococcal origin and suited for a utility purpose.

The plasmid pVS2 according to the invention is based on a ClaI fragment of 1.7 kb from the *S. lactis* cryptic plasmid pSH71(3). A chloramphenicol resistance gene from the *S. sanguis* plasmid pGB301(1) and an erythromycin resistance gene from the *Staph. aureus* plasmid pE194 (14) are inserted therein. Between these resistance regions there is a fragment of 0.35 kb from the *E. coli* vector pBR322 (12). The total size of the plasmid is 5.0 kb.

The plasmid pVS2 contains the following individual restriction sites: ClaI, BclI, HindIII and BstEII. Moreover, two HpaII sites are found between HindIII and BstEII at a distance of nine base pairs from each other so that in practice they form a single restriction site. The cleaving point of BclI is positioned in the erythromycin resistance gene and the BstEII site in the chloramphenicol resistance gene, so that these two sites are insertional inactivation sites.

Since the erythromycin resistance region is positioned between the ClaI and HindIII sites, the erythromycin resistance gene can be inactivated or deleted, not only by a simple BclI digestion but also by a double digestion by ClaI-BclI, BclI-HindTTI. ClaI-HindIII, ClaI-HpaII and BclI-HpaII.

Since DNA cleaved by the enzymes ClaI, HpaII, TagI, AccI and AcyI can be inserted in the restriction sites ClaI and HpaII and, correspondingly, DNA fragments obtained by the enzymes BamHI, BalI, BglII, MboI, SauIIIA and XhoII in the restriction site BclI, the erythromycin resistance region of pVS2 is extremely suitable for "forced cloning". In this method the free DNA ends of both the fragment to be cloned and the cloning vector are formed by two different enzymes. The vector can, for instance, be cleaved by the enzymes ClaI and BclI, the ends of the fragment to be cloned being of the form HpaII and BamHI. If desired, the "forced cloning" method may also be applied to the chloramphenicol resistance region utilizing the BstEII-HpaII or BstEII-HindIII double digestions. The Streptococcus lactis strain VS 135, containing the vector plasmid pVS2, is deposited under the number DSM 3749 in the deposition authority Deutsche Sammlung von Mirkroorganismen Grisebachstrasse 8, D-3400 Gööttingen, FRG. The deposit date is June 2, 1986.

DESCRIPTION OF THE FIGURE

The figure illustrates the construction of the plasmid pVS2. (The restriction enzyme recognition sites essential for the construction are indicated in the plasmids. The recognition sites are based on the restriction maps published previously on the plasmids (References 1, 3, 12 and 14), with the exception of the ClaI sites of the plasmids pGB301and pSH71, which were determined during the construction.)

MATERIAL AND METHODS (1) Plasmids and their isolation

Figure 1:
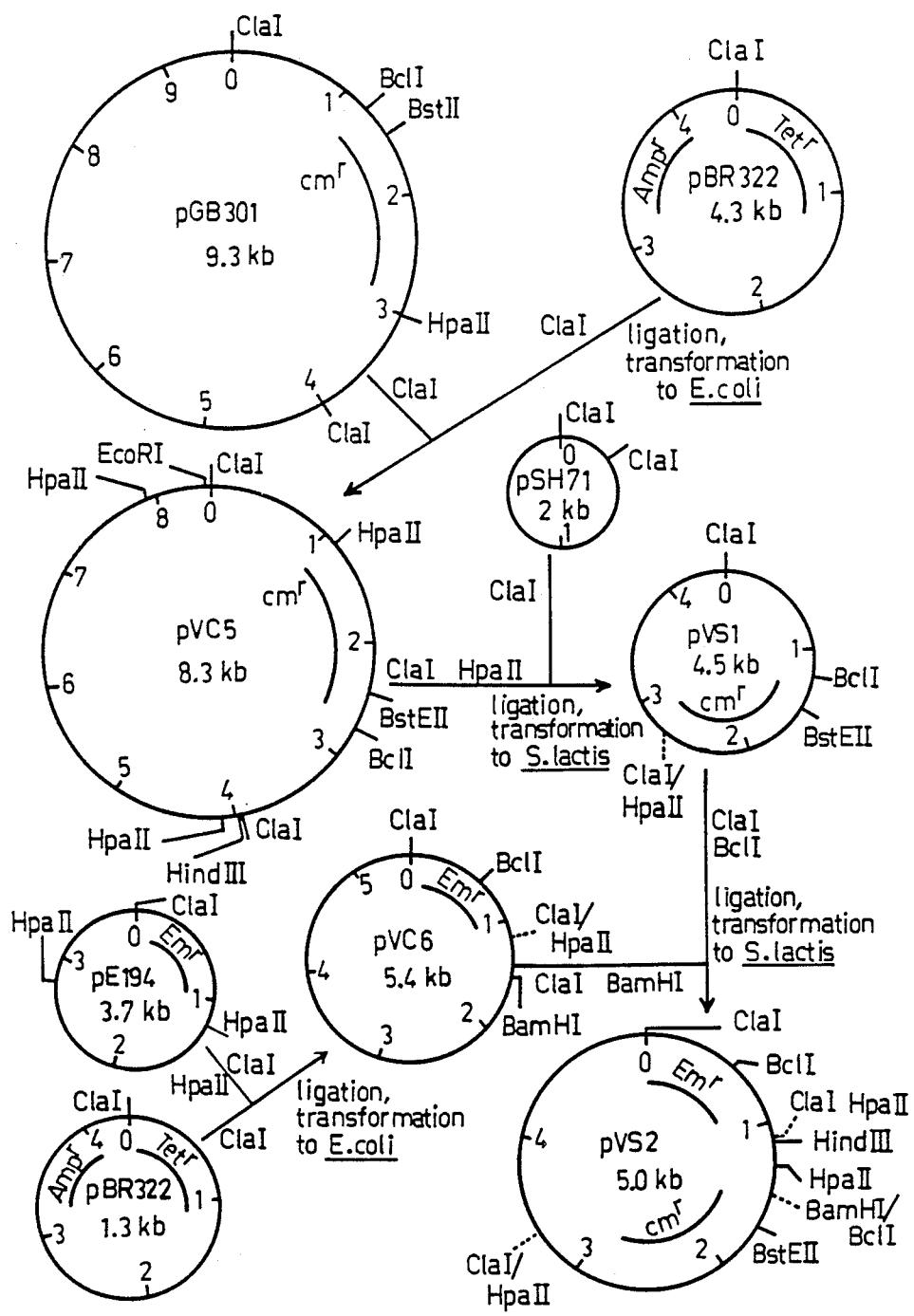

The plasmids and the host strains thereof used for the construction of the plasmid pVS2 are shown in Table 1. The plasmids were isolated from streptococci by the method of Gasson (3), from *E. coli* by the method of Birnboim (2) and from *Staph. aureus* by the method of Guerry et al. (5).

(2) Media

M17 broth or agar supplemented with glucose (13) was used as a growth medium for streptococci. In the treatment of protoplasts, 0.4 M sucrose was used as an osmotic stabilizer. *E. coli* was grown in LB broth or on LB agar prepared according to Maniatis et al. (8).

(3) Restriction enzymes and DNA ligase

The restriction enzymes and the T-4-DNA ligase used were obtained from Boehringer-Mannheim (FRG), and they were used according to the instructions of Maniatis et al. (8).

TABLE 1

| Plasmids used for the construction of the vector pVS2 and the host strains of these plasmids | | | | | |
|---|---|---|---|---|---|
| Plasmid | Size of plasmid (kb) | Selection genes | Reference | Host Strain | Origin of strain |
| pSH71 | 2.1 | Cryptic | 3 | *S. lactis* MG1365 | M. Gasson, The National Institute for Research in Dairying, Reading, England |
| pGB301 | 9.3 | $Cm^r Em^r$ | 1 | *S. lactis* VS118 | A strain from Valio, described in Reference 15 |
| pE194 | 3.7 | $Em^r$ | 14 | *Staph. aureus* RN2442 | R. Novick, The public Health Research Institute of the City of New York Inc., New York, USA |
| pBR322 | 4.3 | $Amp^r Tet^r$ | 12 | *E. coli* RN4378 | |

$Amp^r$ = ampicillin resistance
$Cm^r$ = chloramphenicol resistance
$Em^r$ = erythromycin resistance
$Tet^r$ = tetracycline resistance
*E. coli* Rn4378 was based on *E. coli* AB259 (9).

(4) Transformation

*E. coli* AB259 (9) and *S. lactis* MG1614 (3) were used as recipient strains in the transformation tests. AB259 was obtained from the Public Health Research Institute of the City of New York Inc. and MG1614 from the National Institute for Research in Dairying (Reading, England). Neither strain has any plasmids of its own.

The standard method of Mandel and Higa according to Maniatis et al. (8) was used in the *E. coli* transformation. The selection media contained ampicillin (50,μg/ml) and either chloramphenicol (5 μg/ml) or erythromycin (50,μg/ml).

The *S. lactis* transformations were carried out as described by v. Wright et al. (15). Either chloramphenicol (5,μg/ml) or erythromycin (2.5,μg/ml) was used for selection.

The invention is illustrated by means of the following examples.

EXAMPLE 1

Cloning of antibiotic resistance genes in *S. lactis* plasmids and construction of the vector pVS2

The different process stages are described in the figure.

From the plasmid pGB301 a fragment of approx. 5 kb containing a chloramphenicol resistance gene was inserted in the *E. coli* vector pBR322 at a ClaI site. This resulted in the plasmid pVC5 of approx. 8.3 kb.

The plasmid pVC5 was double-digested by the enzymes ClatI and HpaII. The resultant fragment of approx. 3.8 kb and containing a chloramphenicol resistance gene was inserted in a 1.7 kb fragment obtained from pSH71 by a ClaI digestion and the resultant recombinant plasmid was transformed in *S. lactis*. The obtained plasmid of 5.5 kb was named pVSl.

An erythromycin resistance gene was isolated from pE194 by cleaving this plasmid by a ClaI-HpaII double digestion and by inserting the resultant fragment of approx. 1.2 kb in pBR322 at the ClaI site. The obtained plasmid was named pVC6.

Finally, pVS1 was digested with the enzymes ClaI and BclI and pVC6 correspondingly with the enzymes ClaI and BamHI. The resultant pVC6-derived ClaI-BamHI fragment of approx. 1.6 kb and containing an erythromycin resistance region was inserted in a 3.3 kb fragment containing the replication genes of pVS1 and a chloramphenicol resistance gene. The resultant hybrid plasmid was used for transformation of *S. lactis*. This resulted in the chloramphenicolerythromycin double resistance plasmid pVS2.

EXAMPLE 2

Transfer of the vector pVS2 to different host bacteria

The transformation in *E. coli* was carried out by standard methods using erythromycin-chloramphenicol plates for selection.

Competent cells of strain BD170 (obtained from the Public Health Research Institute of the City of New York Inc.) were used as recipients in the transformation in *B. subtilis*. Chloramphenicol (5 $\mu$g/ml) was used for selection.

Both *E. coli* and *B. subtilis* were transformed well with the plasmid pVS2, and both of the resistance genes of the plasmid were expressed in these hosts.

The plasmid pVS2 was transferred into the *Streptococcus cremoris* SSC179 and *S. lactis* subsp diacetylactis SSD194 strains by protoplast transformation using the same methods as with the *S. lactis* MG1614 strain. Chloramphenicol resistance was used for selection. The transformation frequences were low ($\sim$100/ug DNA with the SSD194 strain, $\sim$10/ug DNA with the SSC179 strain). All the transformants were resistent to erythromycin, and the new plasmid corresponding to pVS2 in size was identified electroforetically from transformants selected at random.

EXAMPLE 3

Cloning of the lactose decomposing genes of the *S. lactis* plasmid pLP712

For the cloning, pVS2 was digested with BclI and the *S. lactis* lactose decomposing plasmid pLP712 (3) with BglII. The resultant BglII fragments were "shot gun" cloned in pVS2 at the BclI sige. The resultant transformants, resistent to chloramphenicol but sensitive to erythromycin, were tested for their lactose decomposing properties. All lactose-positive transformants contained a plasmid of approx. 20 kb. Accordingly, the lactose decomposing genes in the plasmid pLP712 are positioned in a BglII fragment B of approx. 15 kb. This corresponds to the preliminary restriction map (3) published on the plasmid.

EXAMPLE 4

Cloning of the *Staph. aureus* thermonuclease gene in *E. coli* and *S. lactis*

The *E. coli* plasmid pFOG301 (11) containing the thermonuclease gene of *Staph. aureus* was digested with the HpaII enzyme, and the resultant fragment of approx. 1.4 kb and containing the thermonuclease gene was "shot gun" cloned in pVS2 at the ClaI site. *E. coli* was transformed with the ligation mixture, and the tranformants were selected using erythromycin-chloramphenicol double digestion. The obtained transformants were tested for thermonuclease activity. DNA was separated from two positive transformants, and *S. lactis* was transformed with the resultant plasmids (both approx. 6.5 kb). Thermonuclease activity was found to be present in all the transformants obtained.

EXAMPLE 5

"Forced cloning" within the erythromycin resistance region

The plasmid pVS2 was digested with the restriction enzymes ClaI and BclI. Correspondingly, the slime-forming plasmid from a milk souring bacteria strain was double-digested digested with the enzymes ClaI and BglII. The DNA's were mixed in the ratio 1:3 and ligated. *S. lactis* MG1614 was transformed with the ligation mixture. The selection was based on the chloramphenicol resistance. The transformants were also tested for erythromycin resistance. Two transformants resistent to chloramphenicol and sensitive to erythromycin were selected for further testing. One of them contained a plasmid of approx. 7.2 kb and the other a plasmid of approx. 10.5 kb. Restriction tests carried out showed that each contained inserted DNA within a region between the ClaI and BclI recognition sites of the plasmid pVS2.

EXAMPLE 6

Inactivation of the chloramphenicol resistance gene by insertion at the BstEII site The plasmid pVS2 was digested with the restriction enzymes HpuII (recognition sites outside the chloramphenicol resistance region) and BstEI (recognition site within the chloramphenicol resistance region). Chromosomal DNA of the *Streptococcus lactis* SSL135 strain was correspondingly digested with the enzymes ClaI and BstEII (double digestions since BstEII is a relatively rare restriction site). The DNA's were mixed in the ratio 1:3 and ligated. *E. coli* was transformed with the ligation mixture and the selection was based on the erythromycin resistance. The resultant transformants were also tested for their chloramphenicol resistance. Six transformants resistent to erythromycin and sensitive to chloramphenicol were selected for further testing. Each contained an insert within the region between the HpaII and BstEII sites of the plasmid pVS2. The sizes of the inserts varied between 0.6 and 5.0 kb.

References

1. Behnke, D. and Gilmore, M. S. (1981) Location of antibiotic resistance determinants, copy control and replication functions of the double selective streptococcal cloning vector pGB301. Mol. Gen. Genet. 184, 115-120.

2. Birnboim, H. C. (1983) A rapid alkaline extraction method for the isolation of plasmid DNA. In Wu, R., Grossman, L., and Moldave, K. (editors) Methods in Enzymology 100, 243-255, Academic Press Inc., New York.

3. Gasson, M. J. (1983) Plasmid complements of *Streptococcus lactis* NCDO712 and other lactic streptococci after protoplast induced curing. J. Bacteriol. 154, 1-9.

4. Gasson, M. J. and Anderson, P. H. (1985) High copy number plasmid vectors for use in lactic streptococci, FEMS Microbiol. Lett. 30, 193-196.

5. Guerry, P., Le Blanc, D. J. and Falkow, S. (1973) General method for isolation of plasmid deoxyribonucleic acid. J. Bacteriol. 116, 1064-1066.

6. Kok, J., van der Vossen, J. M. B. M. and Venema, G. (1984) Construction of plasmid cloning vector for lactic streptococci which also replicate in *Bacillus sub-* tilis and *Escherichia coli*. Appl. Environ, Microbiol. 48, 726–731.

7. Kok, J., von Dijl, J. M., van der Vossen, J. M. B. M. and Venema, G.,(1985) Cloning and expression of a *Streptococcus cremoris* proteinase in *Bacillus subtilis* and *Streptococcus lactis*. Appl. Envison, Microbiol. 50, 94–101.

8. Maniatis, T., Fritsch, E. F. and Sambrook, J. (1982) Molecular cloning, a laboratory manual, Cold Spring Harbor Laboratory.

9. Marinus, M. G. (1973) Location of DNA methylation genes of the *Escherichia coli* K-12 genetic map. Mol. Gen. Genet. 127, 47–55.

10. McKay, L. L. (1983) Functional properties of plasmids in lactic streptococci. Antoine van Leeuwenhoek 49, 259–274.

11. Shortle, D. (1983) A genetic system for analysis of *staphylococcal nuclease*. Gen. 22, 181–189.

12. Sutcliffe, J. G. (1978) pBR322 restriction map marked from the DNA requence: Accurate DNA size markers up to 4361 nucleotide pairs long. Nucleic Acids Res. 5, 2721.

13. Terzaghi, B. E. and Sandine, W. E. (1975) Improved medium for lactic streptococci and their bacteriophages. Appl. Microbiol. 29, 807–813.

14. Weisblum, B., Graham, M. Y. and Dubnau, D. (1979) Plasmid copy number control: Isolation and characterization of high copy-number mutants of plasmid pE194. J. Bacteriol. 137, 635–643.

15. von Wright, A., Taimisto, A. -M. and Sivelä, S. (1985) Effect of $Ca^{2+}$ ions on the plasmid transformation of *Streptococcus lactis* protoplasts. Appl. Environ. Microbiol. 50, 1100–1102.

We claim:
1. Plasmid pVS2.
2. A microorganism transformed with plasmid pVS2.

* * * * *